«12» United States Patent
Tadepalli et al.

(10) Patent No.: US 8,269,054 B2
(45) Date of Patent: Sep. 18, 2012

(54) PROCESS FOR PRODUCING TETRA-HYDRO ALKYL SUBSTITUTED INDANES

(75) Inventors: Sunitha Rao Tadepalli, Manalapan, NJ (US); Geatesh Karunakaran Tampy, Colts Neck, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 506 days.

(21) Appl. No.: 12/621,647

(22) Filed: Nov. 19, 2009

(65) Prior Publication Data
US 2011/0118519 A1 May 19, 2011

(51) Int. Cl.
*C07C 13/28* (2006.01)

(52) U.S. Cl. .......... 585/360; 585/430; 585/431
(58) Field of Classification Search .......... None
See application file for complete search history.

(56) References Cited

U.S. PATENT DOCUMENTS 2,896,001 A * 7/1959 Edwards et al. .......... 585/447
2011/0077440 A1 * 3/2011 Lawal et al. .......... 585/360

* cited by examiner

*Primary Examiner* — Tam M Nguyen
(74) *Attorney, Agent, or Firm* — Elizabeth M. Quirk; XuFan Tseng; Joseph F. Leightner

(57) ABSTRACT

The present invention relates to an improved process for producing tetra-hydro alkyl substituted indanes which are used in the synthesis of fragrance ingredients for perfumery applications.

12 Claims, 1 Drawing Sheet

Microreactor Setup for the production of tetra-hydro alkyl substituted indanes

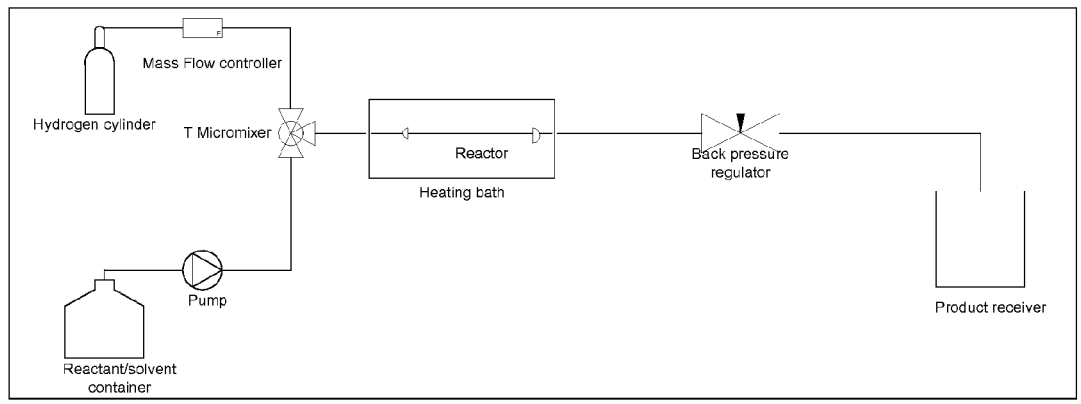
Microreactor Setup for the production of tetra-hydro alkyl substituted indanes

PROCESS FOR PRODUCING TETRA-HYDRO ALKYL SUBSTITUTED INDANES

FIELD OF THE INVENTION

The present invention relates to an improved process for conducting hydrogenation of alkyl substituted indanes to produce tetra-hydro alkyl substituted indanes which are key intermediates in the synthesis of fragrance ingredients for perfumery applications.

BACKGROUND OF THE INVENTION

Tetra-hydro alkyl substituted indanes are key ingredients in the synthesis of musk and woody fragrance ingredients. These compounds are formed from selective hydrogenation of alkyl substituted indanes in the presence of platinum group metal catalyst. Conventionally, these hydrogenation reactions are conducted in batch reactors such as high pressure autoclaves. The reaction kinetics of fast hydrogenation are often limited by external mass transfer of gas through the liquid to the catalyst surface on account of the poor gas/liquid/solid contact provided by these reactors. As a result, reactions take much longer time than kinetically required, leading to side reaction(s) and formation of significant amount of byproduct(s). Besides, these reactions are highly exothermic in nature. Poor heat transfer may lead to non-uniform temperature distribution in the reactors, which may also have deleterious effects on the reactor performance such as the formation of hot-spots and thermal runaway conditions.

In recent years, the use of microreactors, also known as microchannel reactors, for enhancing the performance of fast hydrogenation reactions has sparked intensive efforts among both academic and industrial participants. Microreactors with their small transverse dimensions possess extremely high surface to volume ratios and consequently exhibit enhanced heat and mass transfer rates. The small transverse dimensions of microreactors enable fast transport across fluid layers thus reducing the reaction time and providing greater selectivity and higher product yield. Besides, the use of a continuous microreactor for highly exothermic reactions enables uniform temperature control throughout the reactor and prevents the occurrence of side reactions that may result due to the existence of temperature gradients inside the reactor. Several patents and articles in the literature disclose the use of microreactor technology for various hydrogenation reactions that have shown improved product yield by taking advantage of enhanced heat transfer or mass transfer rates. Microreactors not only help to improve the product yield and Space Time Yield or productivity but also offer cleaner, safer and more energy efficient technology to the perfumery industry which is constantly searching for safe, high-throughput production methods with reduction in energy consumption and minimization of liability risks compared to the existing batch reactors.

The present invention involves using the advantages of microreactors for the synthesis of tetra-hydro alkyl substituted indanes known as THPMI from the selective hydrogenation of alkyl substituted indanes known as PMI, wherein THPMI constitutes a mixture of 2 isomers: tetra-hydro penta-methyl indane and tetra-hydro ethyl tri-methyl indane, and PMI constitutes a mixture of 2 isomers: penta methyl indane and ethyl tri-methyl indane.

SUMMARY OF THE INVENTION

The present invention provides an improved process for the production of tetra-hydro alkyl substituted indanes, wherein the process comprises the step of reacting a gas stream containing hydrogen with a liquid stream containing alkyl substituted indanes on a catalyst in a microreactor. According to the present invention, the microreactor improves the product yield and Space Time Yield or productivity, and makes the process highly energy efficient.

DETAILED DESCRIPTION OF THE INVENTION

According to one embodiment of the invention, a process for the production of tetra-hydro alkyl substituted indanes is provided, which comprises the step of reacting a gas stream containing hydrogen with a liquid stream containing alkyl substituted indanes on a catalyst in a microreactor.

The tetra-hydro alkyl substituted indanes may be, but not limited to, tetra-hydro penta-methyl indane or tetra-hydro ethyl tri-methyl indane.

As used herein, the term "reactor" refers to a device where the reaction actually occurs. As used herein, both terms "microreactor" and "microchannel reactor" refer to a device or an assemblage of related devices that contains reaction channels in which at least one of the transverse dimensions is sub-millimeter.

The microreactor may be a packed bed reactor, which is packed with a packing material such as a catalyst and/or glass beads (having a particle size from about 10 to about 100 $\mu$m). As used herein, the term "packed" means to fill with an amount of the packing material that allows effective production of a pre-determined amount of tetra-hydro alkyl substituted indanes, wherein the amount often requires taking into consideration, e.g., the sizes of the microreactor reaction channels, the type of the packing material, and the pre-determined amount of tetra-hydro alkyl substituted indanes.

Suitable catalysts for producing the tetra-hydro alkyl substituted indanes may comprise at least one metal on a support. The metal in the catalyst may belong to the platinum group such as palladium, platinum, iridium, osmium, rhodium or ruthenium. In such embodiments, the support of the catalyst may comprise a silica compound, an alumina compound, a carbon compound or a combination thereof. The catalyst can be commercially available or made in-house. In such embodiments, the concentration of metal in the catalyst may vary from about 0.1 to about 10 wt %.

The process in the microreactor may be carried out at a temperature from about 100 to about 220° C. and a pressure from about 300 to about 1000 psig.

The liquid stream may comprise a solvent including, but not limited to, hydrocarbons such as hexane, decane, cylcohexane, decalin; a mixture of hydrocarbons such as isopars; alcohols such as methanol, ethanol, iso-propyl alcohol; and ketones such as acetone, methyl ethyl ketone. In such embodiments, the concentration of the solvent in the liquid stream may vary from about 10 to about 90 wt %. The mole ratio of hydrogen to the alkyl substituted indanes may vary from about 0.5 to about 10.

The process for the production of tetra-hydro alkyl substituted indanes is illustrated by, but not limited to, the following experimental procedure and FIG. 1. The liquid stream containing alkyl substituted indane isomers and/or solvent is pumped into the microreactor. The gas stream containing hydrogen is mixed with the liquid stream in a tee (i.e., a T-junction, which is a point where one means of delivery meets another without crossing it, thus, forming a "T" between them) before entering the microreactor. The microreactor may comprise channels with internal diameter (ID) ranging from about 0.5 to about 3 mm. The microreactor may be packed with inert a catalyst and/or glass beads and placed in a heating circulating oil bath. From the microreactor, the reaction mixture is collected in a product receiver. The setup may comprise a back pressure regulator after the microreactor to obtain the desired back pressure for the reaction. The reaction mixture is analyzed using Gas Chromatography (GC).

The process of the present invention provides a high-energy efficiency, wherein the energy efficiency is measured from the rate of heat removed from the microreactor during the reaction. As used herein, "high-energy efficiency" refers to a high heat removal rate per volume of the microreactor in the microreactor process compared to a batch process.

The following are provided as specific embodiments of the present invention. Other modifications of this invention will be readily apparent to those skilled in the art. Such modifications are understood to be within the scope of this invention. All the reactants and solvents were obtained as commercial grade from IFF production plants. As used herein all percentages are weight percent unless otherwise noted, L is understood to be liter, mL is understood to be milliliter, psig is understood to be pounds per square inch guage, g is understood to be gram, min is understood to be minutes and hr to be hour. Productivity of PMI is expressed as the Space Time Yield or average reaction rate (ARR) and the yield is calculated as:

$$ARR = \frac{x_{prod} \cdot F_{reactants}}{w_g}$$

$$Yield = \frac{Amount\ of\ product\ formed}{Total\ amount\ of\ reactants\ fed\ in\ the\ reactor}$$

Residence time is calculated as, $$Residence\ time = \frac{\varepsilon V_{MR}}{F_{reactants}}$$

Energy removal rate is calculated as, $$Energy\ removal\ rate = \frac{Heat\ of\ reaction \cdot ARR \cdot \rho \cdot 1000}{Molecular\ weight\ of\ product \cdot 3600}$$

wherein $x_{prod}$ is weight fraction, $F_{reactants}$ is mass flow rate of reactants into the microreactor (g/hr), $w_g$ is the weight of catalyst (g), $\varepsilon$ is the fractional void space of the packed bed, $V_{MR}$ is the volume of the microreactor (L), $\rho$ is the amount of catalyst per unit volume of the microreactor (g/L), Heatofreaction is Heat of reaction (kJ/mole) and Molecularweightofproduct is Molecular weight of product (g/mole). IFF as used herein is understood to mean International Flavors & Fragrances Inc., New York, N.Y., USA.

EXAMPLE 1

Production of THPMI in a Microreactor Using a Commercial Palladium Catalyst (Commercially Available from Degussa Corporation, Calvert City, Ky.):

150 mg of 5 wt % Pd on carbon (Catalyst A) was packed into a microreactor having a length of 15 cm and an inner channel diameter of 2.4 mm. 40 sccm of hydrogen gas and 0.05 ml/min of liquid reactant (PMI) were fed into the microreactor which was maintained at a temperature of 185° C. and an average pressure of 700 psig. The residence time in the microreactor was ~12 seconds. The concentration of THPMI in the product mixture (analyzed by GC) was ~61 wt % with a Space Time Yield or average reaction rate of 11.4 g product/g catalyst hr. The energy or heat removal rate in the microreactor under these conditions was 655 kW/m$^3$.

Production in a Plant Reactor:

In a 2 m$^3$ pressure reactor, 2250 kg of PMI and 20 kg of Catalyst A were charged. The reactor was maintained at a reaction temperature of 185° C., a pressure under 700 psig hydrogen, and a power to volume ratio of 2.1 kW/m$^3$ for 20 hrs (reaction time). The concentration of THPMI in the product mixture (analyzed by GC) at the end of the reaction was ~57 wt % with a Space Time Yield of 3.3 g product/g catalyst hr. The energy or heat removal rate in the microreactor under these conditions was 9 kW/m$^3$.

EXAMPLE 2

Production of THPMI in a Microreactor Using Another Commercial Palladium Catalyst (Commercially Available from Johnson Matthey, West Deptford, N.J.):

110 mg of 5 wt % Pd on carbon (Catalyst B) was packed into a microreactor having a length of 15 cm and an inner channel diameter of 2.4 mm. 36 sccm of hydrogen gas and 0.04 ml/min of liquid reactant (PMI) were fed into the microreactor, which was maintained at a temperature of 165° C. and an average pressure of 700 psig. The residence time in the microreactor was ~14 seconds. The concentration of THPMI in the product mixture (analyzed by GC) was ~67 wt % with a Space Time Yield or average reaction rate of 13.7 g product/g catalyst hr. The energy or heat removal rate in the microreactor under these conditions was 537 kW/m$^3$.

EXAMPLE 3

Production of THPMI in a Microreactor Using Solvent:

110 mg of Catalyst B was packed into a microreactor having a length of 15 cm and an inner channel diameter of 2.4 mm. 40 sccm of hydrogen gas and 0.14 ml/min of liquid reactant and solvent (25 wt % PMI in IsoPar-H) were fed into the microreactor, which was maintained at a temperature of 165° C. and at an average pressure of 750 psig. The residence time in the microreactor was ~11 seconds. The concentration of THPMI in the product mixture (analyzed by GC) was ~73 wt % with a Space Time Yield or average reaction rate of 12.3 g product/g catalyst hr. The energy or heat removal rate in the microreactor under these conditions was 453 kW/m$^3$.

What is claimed:

1. A process for the production of a tetra-hydro alkyl substituted indane, the process comprising the steps of reacting a liquid stream containing an alkyl substituted indane with a gas stream containing hydrogen in the presence of a catalyst in a microreactor system and producing the tetra-hydro alkyl substituted indane.

2. The process of claim 1, wherein the tetra-hydro alkyl substituted indane is tetra-hydro penta-methyl indane or tetra-hydro ethyl tri-methyl indane.

3. The process of claim 1, wherein the microreactor system comprises a channel with a diameter ranging from about 0.5 to about 3 mm.

4. The process of claim 1, wherein the microreactor system is a packed bed reactor comprising of a packing material selected from the group consisting of a glass bead, a catalyst, and a mixture thereof.

5. The process of claim 4, wherein the glass bead has a particle size ranging from about 10 to about 100 μm.

6. The process of claim 1, wherein the catalyst comprises a platinum group metal.

7. The process of claim 6, wherein the platinum group metal is selected from the group consisting of palladium, platinum, iridium, osmium, rhodium, ruthenium and a mixture thereof.

8. The process of claim 1, wherein the mole ratio of hydrogen to the alkyl substituted indane ranges from about 0.5 to about 10.

9. The process of claim 1, wherein the process is carried out at a temperature ranging from about 100 to about 220° C.

10. The process of claim 1, wherein the process is carried out at a reaction pressure ranging from about 300 to about 1000 psig.

11. The process of claim 1, wherein the liquid stream comprises a solvent selected from the group consisting of hexane, decane, cylcohexane, decalin, an isopar, methanol, ethanol, iso-propyl alcohol, acetone, and methyl ethyl ketone.

12. The process of claim 11, wherein the solvent has a concentration ranging from about 10 to about 90 wt %.

\* \* \* \* \*